US012259356B2

(12) United States Patent
Oh et al.

(10) Patent No.: US 12,259,356 B2
(45) Date of Patent: Mar. 25, 2025

(54) METHOD AND COMPOSITION FOR QUANTIFYING PROTEIN USING TAGGED STANDARDS

(71) Applicant: Bio-Rad Laboratories, Inc., Hercules, CA (US)

(72) Inventors: Kenneth Oh, Pleasant Hill, CA (US); Carl Marlowe, San Francisco, CA (US); Stephen L. Swihart, Walnut Creek, CA (US); Evan Thrush, San Anselmo, CA (US); Michael Griffin, El Cerrito, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 306 days.

(21) Appl. No.: 17/544,591

(22) Filed: Dec. 7, 2021

(65) Prior Publication Data

US 2022/0178874 A1 Jun. 9, 2022

Related U.S. Application Data

(60) Provisional application No. 63/122,467, filed on Dec. 7, 2020.

(51) Int. Cl.
*G01N 27/447* (2006.01)
*G01N 21/64* (2006.01)
(Continued)

(52) U.S. Cl.
CPC ... *G01N 27/44726* (2013.01); *G01N 21/6456* (2013.01); *G01N 33/6827* (2013.01); *G01N 2021/6439* (2013.01)

(58) Field of Classification Search
CPC .................................................. G01N 21/64
See application file for complete search history.

(56) References Cited

U.S. PATENT DOCUMENTS 9,663,554 B2   5/2017   Padhye et al.
9,766,206 B2   9/2017   Yang et al.
(Continued)

FOREIGN PATENT DOCUMENTS

WO   2011031497 A2   3/2011
WO   2011068340 A2   6/2011
(Continued)

OTHER PUBLICATIONS

Barnett, Samuel FH, Mary Snape, C. Neil Hunter, Miguel A. Juárez, and Ashley J. Cadby. "A novel application of non-destructive readout technology to localisation microscopy." Scientific Reports 7, No. 1 (2017): 42313. (Year: 2017).*

(Continued)

*Primary Examiner* — Elizabeth A Robinson
*Assistant Examiner* — Brittany I Fisher
(74) *Attorney, Agent, or Firm* — Kolisch Hartwell, P.C.

(57) ABSTRACT

Methods and reference compositions for quantifying protein using tagged standards. In an exemplary method, a reference composition and a protein may be electrophoresed in respective lanes of a gel. The reference composition may include quantitation standards of different size and each including a tag present at a different concentration. The quantitation standards and the protein may be transferred from the gel to a solid support to create a blot. Luminescence may be detected from the blot to obtain respective luminescence values separately representing an abundance of the tag of each quantitation standard and an abundance of the protein. A quantity of the protein may be determined using the respective luminescence values.

13 Claims, 8 Drawing Sheets

(51) Int. Cl.
*G01N 33/58* (2006.01)
*G01N 33/68* (2006.01)

(56) References Cited

U.S. PATENT DOCUMENTS

| | | |
|---|---|---|
| 2009/0023156 A1 | 1/2009 | Voss et al. |
| 2012/0104267 A1 | 5/2012 | Matsumoto et al. |
| 2014/0004533 A1* | 1/2014 | Siino, Jr. ............ G01N 33/6839 435/7.9 |
| 2014/0311909 A1* | 10/2014 | Siino, Jr. ............ G01N 33/6803 204/461 |
| 2017/0016829 A1 | 1/2017 | Swihart et al. |
| 2017/0107562 A1* | 4/2017 | Rothberg ............ C12Q 1/6874 |
| 2019/0186987 A1 | 6/2019 | Barak |

FOREIGN PATENT DOCUMENTS

| | | |
|---|---|---|
| WO | 2012149180 A2 | 11/2012 |
| WO | 2013163451 A1 | 10/2013 |
| WO | 2014004959 A1 | 1/2014 |
| WO | 2020237095 A1 | 11/2020 |

OTHER PUBLICATIONS

Rodriguez, Karl, Authorized Officer, Commissioner for Patents, U.S. Patent and Trademark Office, "International Search Report" in connection with related International Application No. PCT/US2021/062221, dated Apr. 15, 2022, 7 pgs.

Rodriguez, Karl, Authorized Officer, Commissioner for Patents, U.S. Patent and Trademark Office, "Written Opinion of the International Searching Authority" in connection with related International Application No. PCT/US2021/062221, dated Apr. 15, 2022, 7 pgs.

Bio-Rad Laboratories, Inc., "Protein Standards Precision Plus Protein WesternC Standards—Versatile, Multi-Application Protein Standards: Colorimetric, Chemiluminescent, and Fluorescent Properties All in One", Bulletin 5561 Rev E, Dec. 20, 2012, 2 pgs.

European Patent Office, "Extended European Search Report" in connection with related European Patent App. No. 21904256.1, dated Jan. 7, 2025, 10 pgs.

Urgan, Michael et al., "Molecular Weight Estimation and Quantitation of Protein Samples Using Precision Plus Protein WesternC Standards, the Immun-Star WesternC Chemiluminescence Detection Kit, and the ChemiDoc XRS Imaging System", Bulletin 5576, Mar. 28, 2011, 6 pgs.

* cited by examiner

METHOD AND COMPOSITION FOR QUANTIFYING PROTEIN USING TAGGED STANDARDS

CROSS-REFERENCE TO PRIORITY APPLICATION

This application is based upon and claims the benefit under 35 U.S.C. § 119(e) of U.S. Provisional Patent Application Ser. No. 63/122,467, filed Dec. 7, 2020, which is incorporated herein by reference in its entirety for all purposes.

INTRODUCTION

Proteins present in samples ("sample proteins") can be resolved from one another by electrophoresis in a polyacrylamide gel, optionally followed by blotting to a solid support to enable more specific and sensitive detection. A set of size markers is typically loaded into one of the wells of the gel and electrophoresed along with sample proteins loaded into other wells of the gel. The set of size markers typically contains a mixture of proteins of different molecular weights, which serve as molecular weight standards against which the molecular weights of the sample proteins are calculated. The size markers only provide molecular weight information to the user, which has been a laboratory convention for decades.

SUMMARY

The present disclosure provides methods and reference compositions for quantifying protein using tagged standards. In an exemplary method, a reference composition and a protein may be electrophoresed in respective lanes of a gel. The reference composition may include quantitation standards of different size each including a tag present at a different concentration. The quantitation standards and the protein may be transferred from the gel to a solid support to create a blot. Luminescence may be detected from the blot to obtain respective luminescence values separately representing an abundance of the tag of each quantitation standard and an abundance of the protein. A quantity of the protein may be determined using the respective luminescence values.

DETAILED DESCRIPTION

Figure 1:
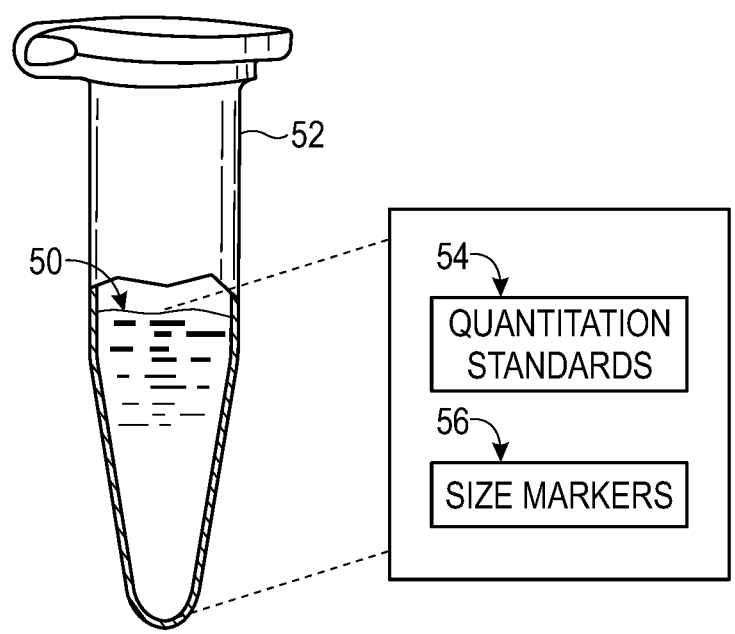
FIG. 1 is a cutaway side view of a vessel holding an exemplary reference composition including a set of tagged quantitation standards for quantifying sample proteins on protein blots and a set of labeled size markers for sizing sample proteins on the protein blots.

The present disclosure provides methods and reference compositions for quantifying protein using tagged standards. In an exemplary method, a reference composition and a protein may be electrophoresed in respective lanes of a gel. The reference composition may include quantitation standards of different size each including a tag present at a different concentration. The quantitation standards and the protein may be transferred from the gel to a solid support to create a blot. Luminescence may be detected from the blot to obtain respective luminescence values separately representing an abundance of the tag of each quantitation standard and an abundance of the protein. A quantity of the protein may be determined using the respective luminescence values.

An exemplary reference composition for protein quantification is provided. The reference composition may comprise a set of size markers configured to be resolved from one another by electrophoresis in a gel to form a ladder representing a series of molecular weights. Each size marker may include a chromophoric or fluorescent label. The composition may include three or more quantitation standards each having a tag. The tags of the three or more quantitation standards may be present at predetermined concentrations defining a concentration range of at least 100-fold.

Total protein present in each sample is often measured in a separate assay prior to gel electrophoresis. For example, a Bradford assay may be performed on samples in order to ascertain the total protein concentration of each sample. The volume of each sample to be loaded into a well of a gel then may be selected such that the same total amount of protein is electrophoresed in each sample lane of the gel. However, this process adds an extra step and is often skipped because it takes time and effort and consumes sample. In contrast, the methods and compositions of the present disclosure enable quantification of sample proteins after they have been electrophoresed in the gel.

Rather than performing Bradford assays, absolute protein quantities in gel and blot assays may be measured by including a series of protein dilutions of known concentration, with which a standard curve can be generated. The standard curve allows a sample protein concentration to be calculated, such as by interpolation or extrapolation. However, this approach generally requires a separate lane of the gel for each protein dilution, which reduces the number of actual samples the user can analyze using the gel. In contrast, the methods and compositions of the present disclosure provide a mixture of tagged quantitation standards of different concentrations for loading in a single lane of a gel. Each of the tagged quantitation standards has a known, calibrated amount of a tag present, the calibrated amounts can be used as the basis for a standard quantitation curve against which the amount of a sample protein is calculated. The tagged quantitation standards can be detected using the same luminescence reagent bound to each of the quantitation standards via the tag thereof. Moreover, the single lane of the gel also can provide molecular weight information using the known molecular weights of the tagged quantitation standards and/or of labeled size markers also present in the lane.

Chemiluminescent reactions decay over time and western blot imaging is typically performed using a single static image. Both of these considerations limit the quantitative value and dynamic range of western blotting results. The present disclosure, in some embodiments, may provide a calibrated set of quantitation standards for use in combination with non-destructive read (NDR) or high dynamic range (HDR) sensors to provide a more sophisticated level of quantitation in western blotting.

Further aspects of the present disclosure are described in the following sections: (I) definitions, (II) reference compositions for protein quantification, (III) methods of quantifying proteins using tagged standards, (IV) examples, and (V) selected aspects.

I. Definitions

Technical terms used in this disclosure have meanings that are commonly recognized by those skilled in the art. However, the following terms may be further defined as follows.

Blot—a solid support including substances, such as proteins, immobilized regionally thereon. The solid support may be described as a planar immobilizing medium or a sheet (i.e., a membrane). The solid support may have any suitable composition such as nitrocellulose, nylon, or polyvinylidene difluoride (PVDF), among others. Used as a verb, the term blot means to transfer or otherwise associate substances with a solid support, such as a membrane.

Label—a molecular structure or a molecule attached (covalently or non-covalently) or otherwise incorporated into a substance, such as a protein, to aid in the detection and/or identification of the substance. A label may be optically detectable directly, or may be detectable indirectly via a luminescence reagent(s). A label that is detectable directly through interaction of the label with light, such as through light absorption or fluorescence, is called an optical label. Exemplary optical labels that may be suitable include photoluminophores (e.g., fluorescent labels) and chromophores (i.e., chromophoric labels, such as light-absorbing, colored dyes, which may be substantially non-fluorescent).

Light—electromagnetic radiation including ultraviolet light, visible light, and/or infrared light. Light interchangeably is called optical radiation.

Luminescence—emission of light from any form of matter, not resulting from heat (i.e., excluding incandescence). Exemplary forms of luminescence that may be suitable for the present disclosure include photoluminescence (e.g., fluorescence) or chemiluminescence. Photoluminescence is light emission from any form of matter in response to the absorption of photons (i.e., photoexcitation). Chemiluminescence is the emission of light from any form of matter resulting from a chemical reaction. Excitation, in chemiluminescence, is caused by a chemical reaction and involves the oxidation of an organic compound, such as luminol, isoluminol, luciferin, or an acridinium ester. The oxidation is performed by an oxidant (e.g., hydrogen peroxide, hypochlorite, oxygen, etc.). The excited product formed in the oxidation reaction emits light. The chemical reaction occurs in the presence of a catalyst, which may be an enzyme (e.g., alkaline phosphatase (ALP) or horseradish peroxidase (HRP), among others), a metal ion or metal complex, or the like. The chemical reaction may be performed in the presence of an enhancer (e.g., a modified phenol, aromatic amine, naphthol, benzothiazole, etc.) to produce enhanced chemiluminescence.

Tag—a label, particularly a label including (i) a binding site for a specific binding partner (e.g., an antibody) and/or (ii) a photoluminophore (e.g., a fluorophore). Exemplary tags include peptide tags, epitope tags, fluorescent tags, etc. Peptide tags include a peptide sequence that is incorporated into a polypeptide genetically, such that the peptide sequence is expressed with the polypeptide. Epitope tags are molecular structures (moieties/sequences) that provide a specific binding site for an antibody, typically a high-affinity antibody. Epitope tags may be peptide tags. Other exemplary tags, such as biotin or fluorescent tags, may be covalently attached to a polypeptide by chemical reaction after the polypeptide has been expressed and isolated.

II. Reference Compositions for Protein Quantification

This section provides an overview of reference compositions comprising tagged quantitation standards; see FIGS. 1-9.

FIG. 1 shows an exemplary reference composition 50 contained in a vessel 52. As depicted schematically in the box to the right of vessel 52, reference composition 50 includes a set of tagged quantitation standards 54 for quantifying sample proteins on protein blots. Optionally, reference composition 50 also includes a set of labeled size markers 56 for sizing sample proteins (and/or quantitation standards 54) on the protein blots. The reference composition may be liquid, such as aqueous, or solid (e.g., lyophilized for reconstitution with liquid by a user), among others.

The set of quantitation standards 54 and/or the set of size markers 56 may have any suitable properties. Any suitable number of quantitation standards 54 and/or size markers 56 may be present in reference composition 50, such as at least one, two, three, four, or five, among others, for each set independently. Each quantitation standard 54 and/or each size marker 56 has a different, predetermined molecular weight that allows the quantitation standard 54 or size marker 56 to be resolved electrophoretically, in a gel, from each other quantitation standard 54 and/or size marker 56 in the set of quantitation standards 54 and/or the set of size markers 56. Each quantitation standard 54 or size marker 56 may be composed of copies of only one type of molecule or may be a mix of two or more types of molecules of similar molecular weight.

Figure 2:
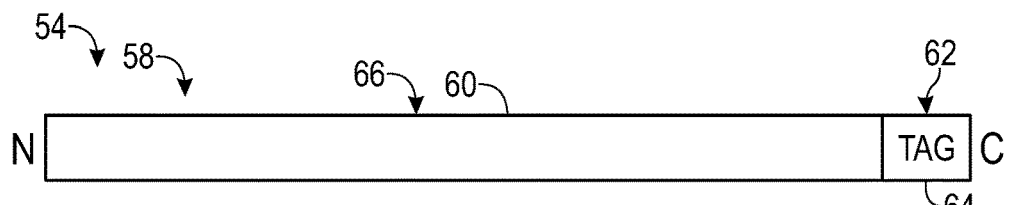
FIG. 2 is a block diagram of an exemplary tagged protein of a quantitation standard for the reference composition of FIG. 1, where the tagged protein has a peptide tag genetically incorporated into a polypeptide of the tagged protein.

FIG. 2 shows an exemplary tagged protein 58 of a quantitation standard 54 for reference composition 50 of FIG. 1. Tagged protein 58 includes a polypeptide 60 and a tag 62 covalently bonded to one another. In the depicted embodiment, tag 62 includes a peptide tag 64 genetically attached to polypeptide 60, such that both polypeptide 60 and peptide tag 64 contribute to the same backbone of tagged protein 58. In other words, polypeptide 60 and peptide tag 64 may be translated from the same messenger RNA to produce a hybrid amino acid sequence 66 including both polypeptide 60 and peptide tag 64.

Figure 3:
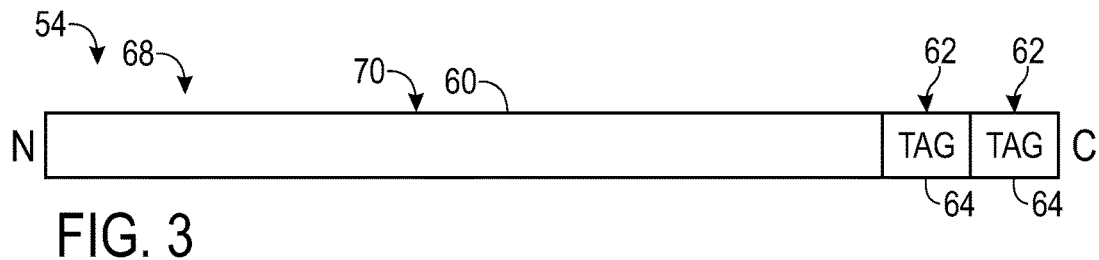
FIG. 3 is a block diagram of another exemplary tagged protein of a quantitation standard for the reference composition of FIG. 1, where the tagged protein is the same as that of FIG. 2 except that the tagged protein has multiple copies of the peptide tag of FIG. 2 genetically incorporated into the polypeptide.

Peptide tag 64 may have any suitable characteristics and location. The peptide tag may contain a sequence of at least three, four, or five amino acids, and/or less than about twenty, fifteen, or ten amino acids, among others. A copy of the peptide tag may be positioned at either end (or both ends) of polypeptide 60, internally along polypeptide 60, intermediate the ends thereof, or a combination thereof. The tagged protein may have any suitable number of copies of peptide tag 64 per molecule, such as only one, as depicted in FIG. 2, or an average of at least two, three, four, five, ten, or more copies per molecule of the tagged protein. For example, FIG. 3 shows a tagged protein 68 having two copies of peptide tag 64 arranged in tandem at the C-terminus of polypeptide 60 to produce a hybrid amino acid sequence 70. In other examples, any suitable number of copies of peptide tag 64 may be separated from one another along polypeptide 60.

Figure 4:
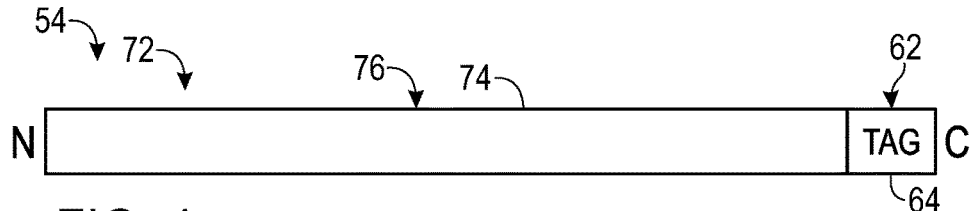
FIG. 4 is a block diagram of another exemplary tagged protein of a quantitation standard for the reference composition of FIG. 1, where the tagged protein has the peptide tag of FIG. 2 genetically incorporated into a different polypeptide of substantially the same size as in FIG. 2.

A given quantitation standard 54 may be a mixture of two or more different molecules of similar, but not identical, size. The use of such a mixture allows each quantitation standard to form a band of distinctive thickness when electrophoresed in a gel, to facilitate identification of the quantitation standard and distinguishing it from other quantitation standards. For example, FIG. 4 shows a tagged protein 72 that may form a quantitation standard in combination with tagged protein 58 of FIG. 2 and/or tagged protein 68 of FIG. 3. Tagged protein 72 may have the same sequence of peptide tag 64 attached to a polypeptide 74 to form a hybrid amino acid sequence 76 that is shorter than hybrid amino acid sequence 66 of tagged protein 58. Polypeptide 74 may have substantial sequence identity with polypeptide 60, such as being a deleted form thereof, or may be substantially unrelated in sequence.

Figure 5:
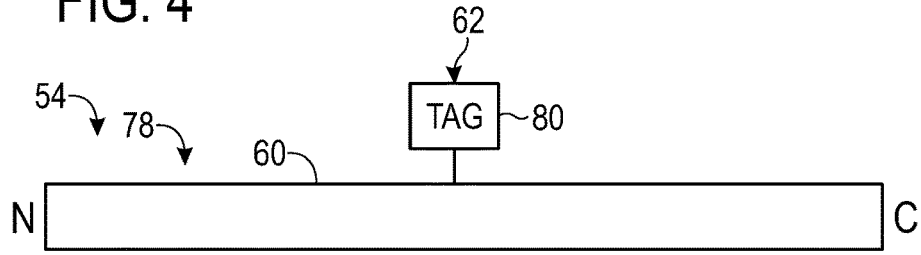
FIG. 5 is a block diagram of yet another exemplary tagged protein of a quantitation standard for the reference composition of FIG. 1, where the tagged protein includes a tag that has been attached to the polypeptide of FIG. 2 (without its tag) after synthesis and isolation of the polypeptide.

FIG. 5 shows another exemplary tagged protein 78 of a quantitation standard 54 for reference composition 50 of FIG. 1. Tagged protein 78, like tagged protein 58 of FIG. 2, has a tag 62 attached to polypeptide 60 of FIG. 2. However, tag 62 of tagged protein 78 is a post-translational tag 80, which may be added to polypeptide 60 by chemical reaction after synthesis of the polypeptide. Post-translational tag 80 may be a fluorescent tag or an epitope tag, among others.

Quantitation standards 54, and particularly tag 62 thereof, may be present at a series of predetermined concentrations (and thus amounts) in reference composition 50. The concentrations differ from one another and may be known relative to one another, and, optionally, may be defined as absolute concentrations. The concentrations may define any suitable range, as the difference (ratio) between the highest and lowest amounts of the quantitation standards (and/or tags thereof), such as a range of at least 10-, 50-, 100-, 200-, 500-, or 1000-fold. The concentrations may be distributed generally uniformly through the range, such as including at least one or at least two quantitation standards falling within each decade (power of ten) of the range. To create the different amounts of a tag 62 in a set of quantitation standards 54, the average number of tag copies present per molecule in each quantitation standard 54 and/or the number of molecules of the quantitation standard may vary among the different quantitation standards 54 of the set.

Figure 6:
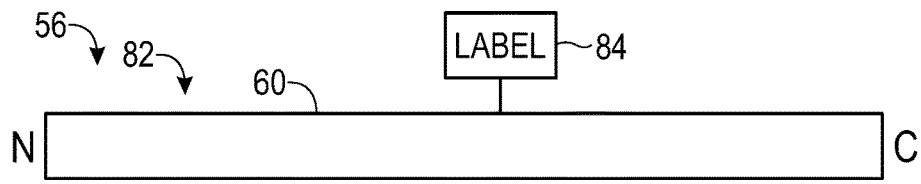
FIG. 6 is a block diagram of an exemplary labeled protein for the reference composition of FIG. 1, where the labeled protein has a label covalently attached to the polypeptide of FIG. 2 (without the peptide tag).

FIG. 6 shows an exemplary labeled protein 82 of a size marker 56 for reference composition 50 of FIG. 1. Labeled protein 82 has a label 84 covalently attached to polypeptide 60 of FIG. 2, but lacks peptide tag 64. Label 84 may be an optical label, such as a fluorescent label or a chromophoric label, among others. Labeled protein 82 (and/or a size marker 56 including the labeled protein) may correspond in size to tagged protein 58 of FIG. 2 (and/or a quantitation standard 54 including the tagged protein), which means that the labeled protein (and/or size marker) and the tagged protein (and/or quantitation standard) migrate at similar velocities during electrophoresis and are less than about 5%, 10%, or 15% different in molecular weight. A size correspondence between one, two, three, or more quantitation markers 54 and the same number of size markers 56 allows the position and/or identity of quantitation markers 54 to be determined based on those of size markers 56.

Figure 7:
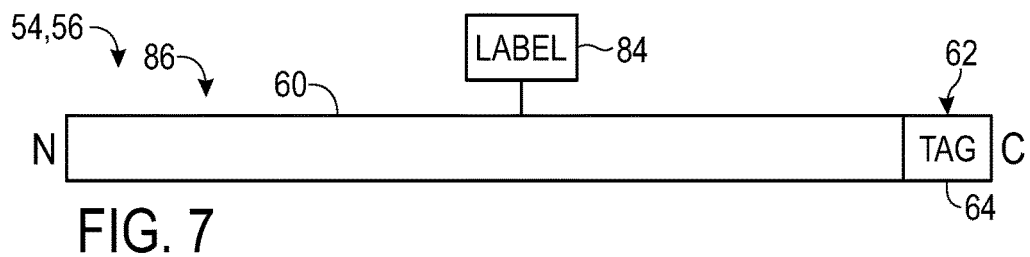
FIG. 7 is a block diagram of an exemplary tagged, labeled protein for the reference composition of FIG. 1, where the tagged, labeled protein has the label of FIG. 6 attached to the polypeptide of FIG. 2, with the peptide tag included.

FIG. 7 shows an exemplary tagged, labeled protein 86 of a quantitation standard 54 and/or a size marker 56 for reference composition 50 of FIG. 1. Tagged, labeled protein 86 has a peptide tag 64 genetically attached to polypeptide 60 of FIG. 2 and a label 84 covalently attached to polypeptide 60, such as post-translationally. A quantitation standard 54 may be composed of tagged, labeled protein 86 alone or may be composed of a mixture of tagged, labeled protein 86 and another tagged protein of similar size, such as tagged protein 58 of FIG. 2. Similarly, a size marker 56 may be composed of tagged, labeled protein 86 alone or may be composed of tagged, labeled protein 86 and another labeled protein of similar size, such as labeled protein 82 of FIG. 6.

Reference composition 50 may have any suitable properties. Each quantitation standard 54 may include the same, structurally identical tag 62, and/or at least each may include a respective tag 62 that is specifically bound by the same specific binding partner. Each of size markers 56, if present in the reference composition, may include a respective label 84 that is chromophoric, or each may include a respective label that is fluorescent. However, in some cases, each size marker 56 may not include the same structurally identical label. For example, size markers 56 may have two or more different chromophoric labels with spectrally different light absorption properties, such that the size markers are labeled using two or more different colors, to facilitate distinguishing and identifying individual size markers of the set.

Size markers 56, and/or a label(s) 84 thereof, may be present at concentrations (and thus amounts) defining a much smaller range than tag 62 of the reference composition. This range of label amount is calculated after correction for differences, if any, in the molar attenuation coefficient (i.e., the light absorptivity) or fluorescence of structurally different labels 84, if any, included in the different size markers 56 of the set of size markers. The range defined by the highest and lowest amounts may be less than 10-fold, to ensure that all of the size markers are visible/detectable at the same time.

Figure 8:
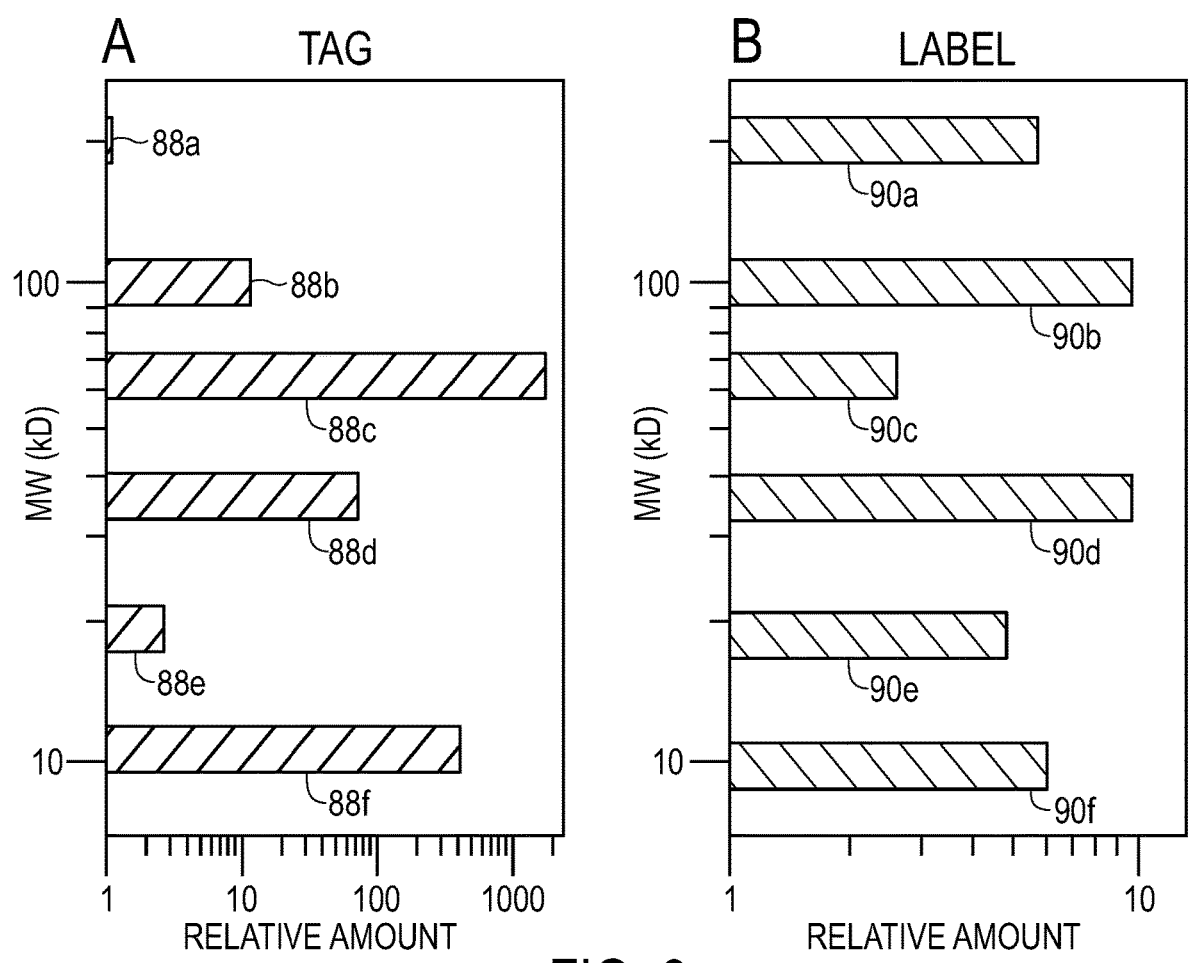
FIG. 8 is a pair of log-log bar graphs plotting, for the reference composition of FIG. 1, exemplary relative amounts of a tag incorporated into each of the quantitation standards (panel A) and exemplary amounts of a label incorporated into each of the size markers (panel B).

FIG. 8 shows a pair of log-log bar graphs plotting exemplary relative amounts of a tag 62 and a label 84 for reference composition 50 of FIG. 1 (also see FIGS. 2-7). Relative amounts 88a-88f of tag 62 incorporated into each tagged quantitation standard 54 of different molecular weight is shown in panel A. The amounts of tag 62 define a concentration range of greater than 1000-fold. Relative amounts 90a-90f of label 84 incorporated into each labeled size marker 56 of different molecular weight is shown in panel B. The amounts of label 84 define a concentration range of only about 5-fold in this illustrative embodiment.

The molecular weights of quantitation standards 54 substantially correspond to those of size markers 56 in the example of FIG. 8. Accordingly, the visible/detectable position of each size marker 56 along a lane of a gel or blot allows a user to infer the position of a corresponding quantitation marker 54 of similar molecular weight. In other examples, only a subset (or none) of the quantitation standards 54 substantially correspond in size to size markers 56, and/or vice versa (see Examples 2-4 of Section IV.

The concentration order in which the amount of tag 62 decreases among quantitation standards 54 may or may not match a molecular weight order (largest to smallest, or smallest to largest) of the quantitation standards. For example, in FIG. 8, the concentration order does not match the molecular weight order. The concentration order from smallest to largest is 88a, 88e, 88b, 88d, 88f, and 88c, respectively, while the molecular weight order for smallest to largest is 88f-88a, respectively.

Figure 9:
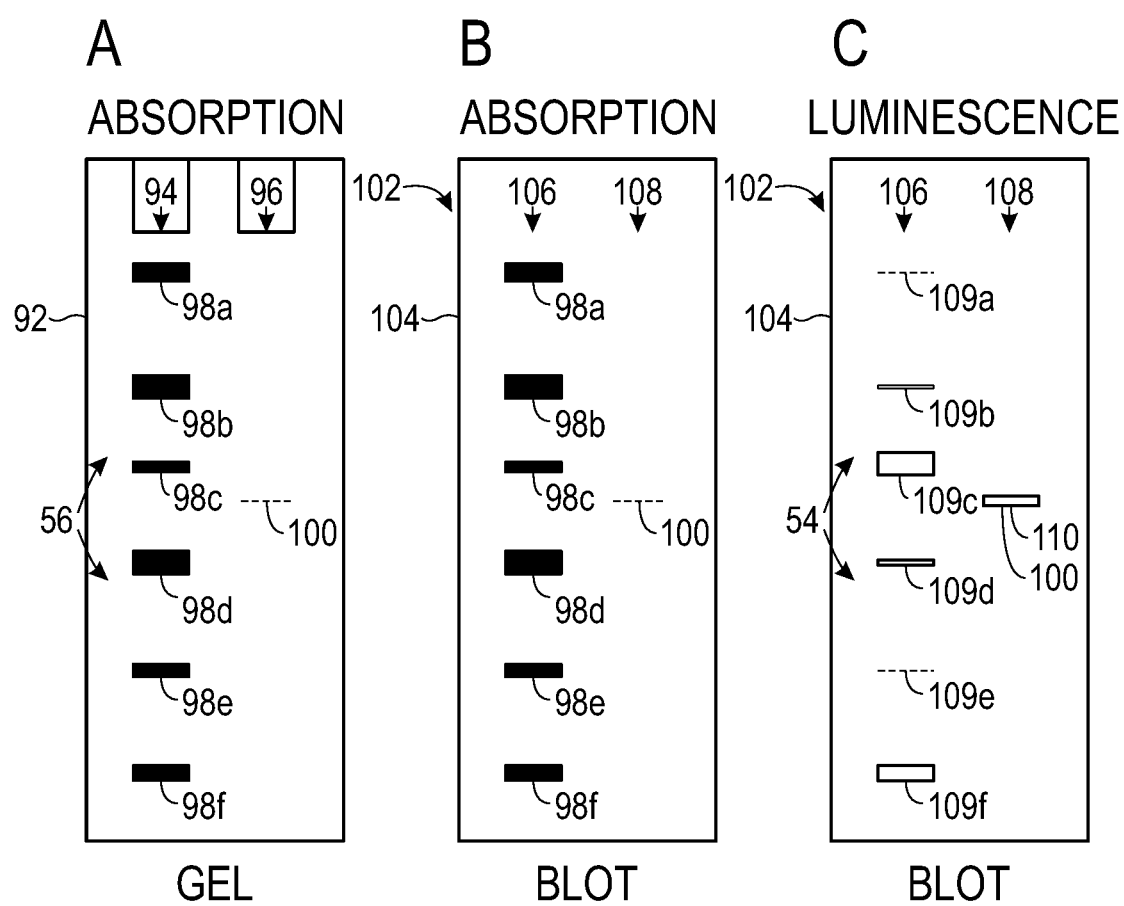
FIG. 9 shows two lanes of a gel in which a reference composition and a sample protein have been electrophoresed (panel A), and a blot produced by transferring the reference composition and sample protein from the gel to a solid support (panels B and C), with absorption of light illustrated in panels A and B and luminescence illustrated in panel C.

FIG. 9 illustrates use of the exemplary reference composition 50 of FIG. 8 in gel electrophoresis, blotting, sizing, and quantifying, where label 84 of size markers 56 is a chromophoric label. Panel A shows an absorption image of a gel 92 having only two lanes, a reference lane 94 and a sample lane 96, extending from corresponding wells. The exemplary reference composition 50 of FIG. 8 has been resolved by electrophoresis in reference lane 94 into a ladder of light-absorbing, size marker bands 98a-98f respectively representing label amounts 90a-90f of size markers 56. A protein-containing sample has been electrophoresed in sample lane 96 of gel 92 adjacent the reference composition to resolve sample proteins of the sample by size. A sample protein 100 of interest is indicated with a dashed line in panel A because sample protein 100 is not labeled and thus not visible. In other embodiments, label 84 may be a fluorescent label(s) and the ladder of size markers may be visible in a fluorescence image of gel 92 instead of an absorption image.

Panel B of FIG. 9 shows an absorption image of a blot 102 generated by transferring size markers 56 of reference lane 94 and sample proteins of sample lane 96 from gel 92 to a solid support 104. Size marker bands 98a-98f are now visible in a reference lane 106 of blot 102. As in panel A, sample protein 100 of interest is not visible in sample lane 108 of blot 102.

Panel C of FIG. 9 shows a luminescence image of blot 102 captured after contacting the blot with a luminescence reagent(s). The luminescence reagent(s) may be configured to facilitate production of photoluminescence (in response to photoexcitation of blot 102) or chemiluminescence representing tagged quantitation standards 54 in reference lane 106 and sample protein 100 in sample lane 108. Accordingly, the luminescence image may be a photoluminescence image or a chemiluminescence image.

Luminescence bands 109a-109f respectively represent quantitation standards 54 of decreasing molecular weight, with the luminescence levels detected indicated by the thickness of each band. The different luminescence levels of luminescence bands 109a-109f respectively correlate with the different tag amounts 88a-88f present in quantitation standards 54 of different molecular weight (compare FIG. 8, panel A, and reference lane 106 of FIG. 9, panel C). The lowest tag amounts 88a and 88e of FIG. 8, panel A, are not detectable in the luminescence image of FIG. 9, panel C, as indicated by dashed lines at 109a and 109e, but may become detectable with a longer exposure (also see Example 5 of Section IV).

Luminescence band 110 represents sample protein 100 in sample lane 108 of blot 102 in panel C of FIG. 9. The luminescence level of luminescence band 110 can be compared with luminescence levels of luminescence bands 109a-109f representing quantitation standards 54, to determine a quantity of sample protein 100 present in the sample.

Further aspects of reference compositions and their use are described below in Sections III-V.

III. Methods of Quantifying Proteins Using Tagged Standards

Figure 10:
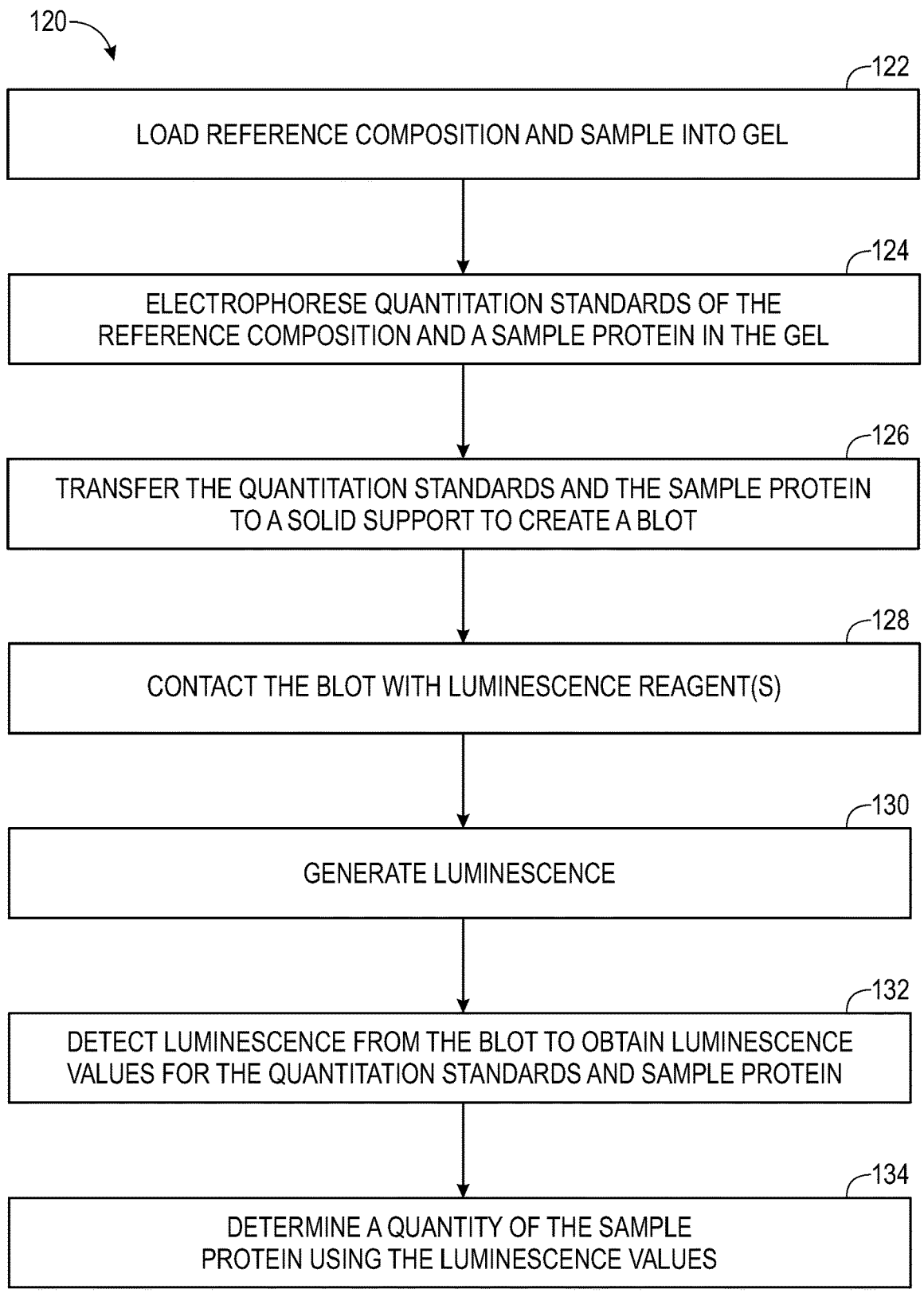
FIG. 10 is a flowchart illustrating exemplary steps that may be performed in a method of quantifying a protein using tagged quantitation standards.

This section provides an overview of exemplary methods of protein quantification using tagged quantitation standards; see FIG. 10.

FIG. 10 is a flowchart illustrating exemplary steps that may be performed in a method 120 of quantifying a protein using luminescence values representing tagged quantitation standards. The steps may be performed in any suitable order and combination and may be modified and supplemented as described elsewhere in the present disclosure.

A reference composition and a sample may be loaded into a gel, indicated at 122. Each may be loaded into a separate well of the gel. The reference composition may have any suitable combination of the properties described in Section II and/or elsewhere in the present disclosure. For example, the reference composition may include two, three, or more quantitation standards each including an identical tag. The concentration of the tag in the reference may vary among the quantitation standards by any suitable order of magnitude (base 10), such as at least one, two, three, four, or five orders of magnitude, among others. The sample includes a sample protein (of interest) and optionally contains a mixture of at least 2, 5, 10, 50, 100, 500, or 1000 different proteins including the sample protein of interest. Additional samples also may be loaded into the gel, with each sample including the sample protein.

The gel may be configured to resolve proteins by size (i.e., molecular weight). Accordingly, the gel may be a polyacrylamide gel, optionally containing a denaturing agent, such as sodium dodecyl sulfate, although other types of gels may be used instead.

The sample protein may have any suitable properties. In some cases, the sample protein may be a proxy for total protein in each sample. For example, the sample protein may be a housekeeping protein that is present at a substantially constant percentage of total protein in different samples. In other cases, the sample protein may have a varying expression level among different samples. For example, in contrast to a housekeeping protein, the expression level of the sample protein may be dependent on the state, identity, origin, health, signaling activity, and/or the like, of the cells from which each sample is prepared.

The quantitation standards of the reference composition and a sample protein of the sample may be electrophoresed in the gel, indicated at 124. The reference composition and the sample protein may be electrophoresed in separate lanes of the gel, with the quantitation standards being resolved from one another in one lane and the sample protein optionally being resolved from one or more other proteins of the sample in another lane. Electrophoresis may be performed while the gel is vertical although other gel orientations, such as horizontal, may be suitable in some cases.

The quantitation standards and the sample protein may be transferred to a solid support to create a blot, indicated at 126. Transfer, also termed blotting, may be performed by application of an electrical potential orthogonal to the gel, to drive proteins from the gel to the solid support. The transfer moves molecules of each quantitation standard and molecules of the sample protein to the solid support, where the molecules may bind to or chemically react with the solid support to become immobilized thereon.

An image of the gel or blot may be captured to detect labeled (e.g., prestained) size markers, if any, in a reference lane of the gel or blot. The image may be an absorption image of the gel/blot if the size markers are labeled with a chromophoric label(s) (e.g., see FIG. 8) or a fluorescence image if the size markers are labeled with a fluorescent label(s). The image may be used to facilitate later sizing and/or identification of luminescence bands representing quantitation standards and the sample protein, by comparing the positions of size marker bands in the image with those of quantitation standard bands in the same image or one or more other images (see below).

The blot may be contacted with one or more luminescence reagents, indicated at 128. A luminescence reagent, as used herein, is a photoluminescent substance, a reactant for a light-emitting chemical reaction, a catalyst for the light-emitting reaction, an enhancer for the light-emitting reaction, or a specific binding partner that connects the photoluminescent substance or the catalyst to one or more proteins of the blot. Exemplary approaches to performing step 128 are described below for photoluminescence and chemiluminescence.

In one photoluminescence approach, quantitation standards 54 in the reference composition 50 each include a photoluminescent tag before electrophoresis. Only the sample protein on the blot needs to be connected to a photoluminescent label. Accordingly, the blot may be contacted with a specific binding partner, such as an antibody, for the sample protein. The specific binding partner may have a photoluminescent label that becomes localized at the sample protein on the blot when the specific binding partner binds to the sample protein, or the photoluminescent label may be connected the sample protein using two or more different specific binding partners arranged in series.

In another photoluminescence approach, one or more (or each) of quantitation standards 54 has a substantially non-photoluminescent tag. Each quantitation standard 54 having the non-photoluminescent tag may be associated with a photoluminescent label by contacting the blot with a tag-specific binding partner for the non-photoluminescent tag of each quantitation standard 54, where the tag-specific binding partner is conjugated to, or otherwise attached or attachable to, a photoluminescent label. The sample protein may be associated with a photoluminescent label using another specific binding partner as described in the preceding paragraph.

In a chemiluminescence approach, the blot is contacted with a set of chemiluminescence reagents. The chemiluminescence reagents include a tag-specific binding partner for the tag present in each quantitation standard. The tag-specific (first) binding partner is configured to connect a catalyst for a light-emitting chemical reaction to the tag. The catalyst may, for example, be an enzyme, such as horseradish peroxidase or alkaline phosphatase. The catalyst may be conjugated to the tag-specific binding protein or connected via an intermediary molecule(s), such as a different specific binding partner. The chemiluminescence reagents also may include a second specific binding partner for the sample protein. The second specific binding partner may be conjugated or otherwise connected to a catalyst (such as via an intermediary molecule(s)). The same catalyst (e.g., horseradish peroxidase) may be used to catalyze the same light-emitting chemical reaction in the reference lane and the sample lane(s) of the blot. The chemiluminescence reagents further may include reactants for the light-emitting chemical reaction (e.g., an oxidizing agent, such as hydrogen peroxide, and a reducing agent, such as luminol).

In a mixed photoluminescence/chemiluminescence approach, the blot is contacted with a suitable combination of the photo- and chemi-luminescence reagents described above. These luminescence reagents may be configured to connect (i) a photoluminescent label to the tag of each quantitation standard and a chemiluminescence catalyst to the sample protein, (ii) a chemiluminescence catalyst to the sample protein (if the quantitation standards already include a photoluminescent tag), or (iii) a chemiluminescence catalyst to each quantitation standard and a photoluminescent label to the sample protein.

Luminescence may be generated, indicated at 130. The luminescence may be generated from areas of the blot at which the quantitation standards and the sample protein are immobilized. The luminescence may be photoluminescence, chemiluminescence, or both. Generating luminescence may include irradiating the blot with excitation light to induce photoluminescence, or incubating the blot at a suitable temperature for the catalyst to catalyze the light-emitting chemical reaction.

Luminescence may be detected from the blot to obtain luminescence values for the quantitation standards and the sample protein, indicated at 132. The luminescence values may include a set of luminescence values each representing an amount of luminescence detected from an area of the blot at which a different one of the quantitation standards is immobilized or from the area of the blot at which the sample protein is immobilized. The amount of luminescence may be detected using any type of sensor, such as an image sensor that captures a luminescence image(s) of the blot, namely a photoluminescence image, a chemiluminescence image, or a mixed photoluminescence/chemiluminescence image (according to the type of tag and luminescence reagents used, as described above). The sensor may be a high dynamic range sensor (having a dynamic range of at $10^2$, $10^3$, or $10^4$, among others) or a non-destructive read sensor, among others. In either case, each luminescence value may represent a luminescence signal integrated spatially over an area of the blot and integrated temporally for a given amount of time, typically the same amount of time for a given set of luminescence values obtained from a captured image. In some cases, a series of luminescence images may be captured from the blot, each representing a different amount of time during which luminescence is detected (e.g., see Example 5 of Section IV).

A quantity of the sample protein may be determined using the luminescence values of the quantitation standards and the sample protein, indicated at 134. A luminescence value(s) of the sample protein may be compared with luminescence values of the quantitation standard. To enable this comparison, a set of luminescence values for the quantitation standards, representing luminescence detected from the blot over the same time period, may be used to produce a standard curve. The luminescence value for the sample protein may be compared with the standard curve to identify a point along the standard curve matching the luminescence value for the sample protein. A quantity value associated with the point may be found to determine the quantity of the sample protein. In some examples, the method may identify/define a linear range of the standard curve.

Comparing the luminescence value for the sample protein with the standard curve may include determining whether the point identified along the standard curve falls within the linear range of the standard curve. If not, the method may compare one or more other luminescence values for the sample protein with one or more other standard curves produced using one or more other sets of luminescence values for the quantitation standards, representing different amounts of detection time, by using the series of luminescence images described above. One of the standard curves, if any, in which the point falls within (or within a threshold distance from) the linear range of the standard curve then may be used to determine the quantity of the sample protein.

The quantitation standards of the reference composition may be calibrated for a given sample protein and luminescence reagent(s), before or during performance of the method, using a known amount of the sample protein. The known amount of the sample protein and the reference composition may be loaded into a gel, electrophoresed, transferred to create a blot, contacted with the luminescence reagent(s), and imaged, as described above, to obtain luminescence values for the known amount of the sample protein and the quantitation standards. The luminescence value of the known amount of sample protein may be compared with the luminescence values for the quantitation standards, such as using a standard curve as described above, to obtain a conversion factor that correlates each quantitation standard with a luminescently-equivalent amount of the sample protein. Stated differently, the conversion factor may be utilized to assign each quantitation standard a respective amount of the sample protein to which the quantitation standard has luminescence equivalence in the method.

Any suitable steps of method 120 may be performed using a computer. A computer-readable medium may store instructions that, when executed by the computer, cause the computer to perform one or more steps of the method, such as steps 130, 132, and/or 134.

IV. Examples

The section describes further aspects of reference compositions comprising quantitation standards, and methods of quantifying protein using the reference compositions. These aspects are presented here for illustration and are not intended to limit the scope of the present disclosure.

Figure 11:
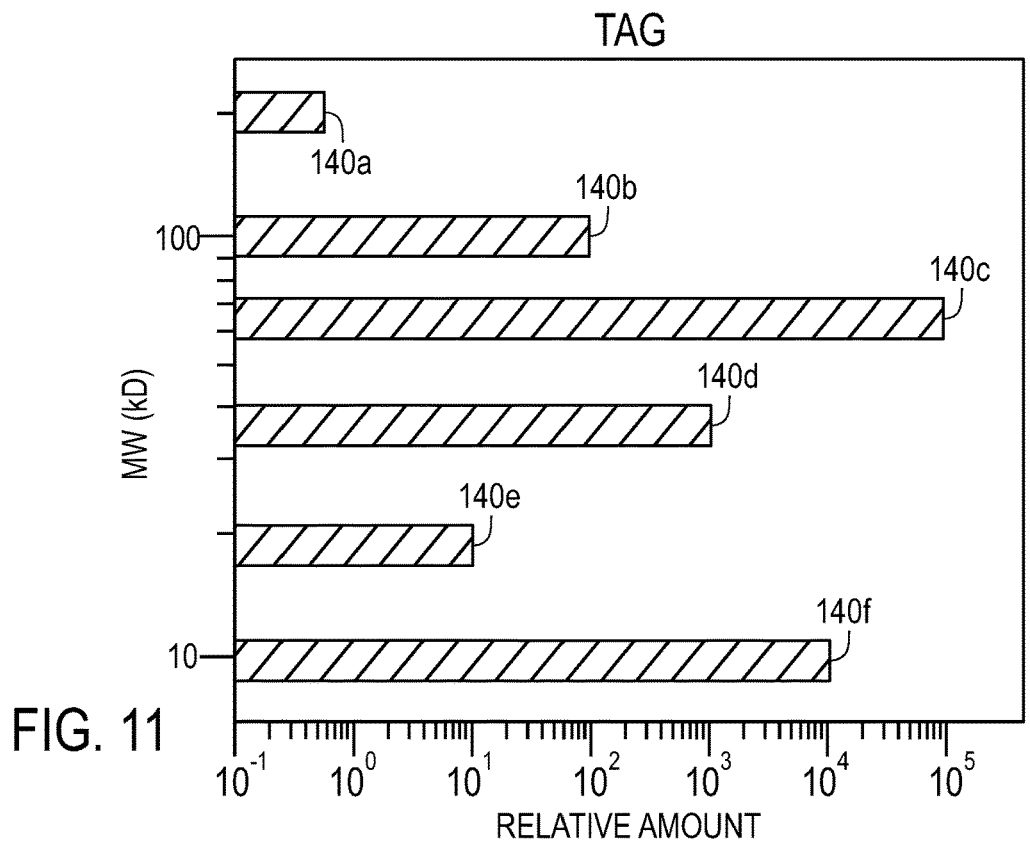
FIG. 11 is a log-log bar graph plotting exemplary relative amounts of a tag incorporated into a set of tagged quantitation standards, where the largest and smallest amounts of the tag differ by a factor of more than $10^5$.

Example 1. Reference Composition with Broad Range of Quantitation Standards This example describes a reference composition having quantitation standards with amounts of the same tag that differ in relative amount by up to five orders of magnitude (base 10); see FIG. 11.

The molecular weights of the quantitation standards are indicated by the respective positions of bars 140a-140f along the MW (molecular weight) axis. The relative amount of the tag present in each quantitation standard is indicated by the length of its corresponding bar and particularly the position along the x-axis of the right end of the bar.

Figure 12:
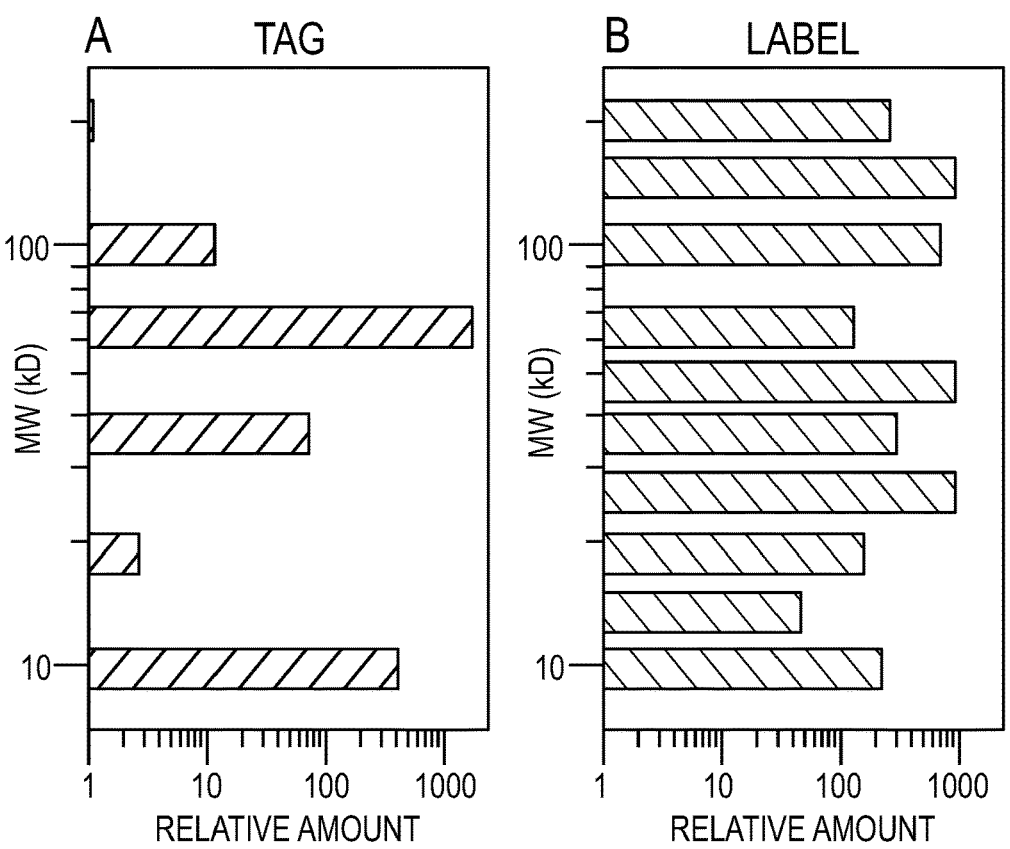
FIG. 12 is a pair of log-log bar graphs plotting, for another exemplary reference composition, relative amounts of a tag present in a set of tagged quantitation standards (panel A) and relative amounts of a label incorporated into a set of labeled size markers (panel B), where only a subset of the labeled size markers correspond in size to one of tagged quantitation standards.

Example 2. Reference Composition with More Size Markers Than Quantitation Standards This example describes a reference composition having a greater number of labeled size markers than tagged quantitation standards of different molecular weight; see FIG. 12.

The reference composition has six tagged quantitation standards (see panel A) and ten labeled size markers (see panel B). Each of the six quantitation standards substantially corresponds in molecular weight to one of the ten size markers. Four of the size markers do not correspond in molecular weight to any of the six quantitation standards. A reference composition with a greater number of size markers than quantitation standards allows the user to more accurately size sample proteins, using the larger number of size markers.

Figure 13:
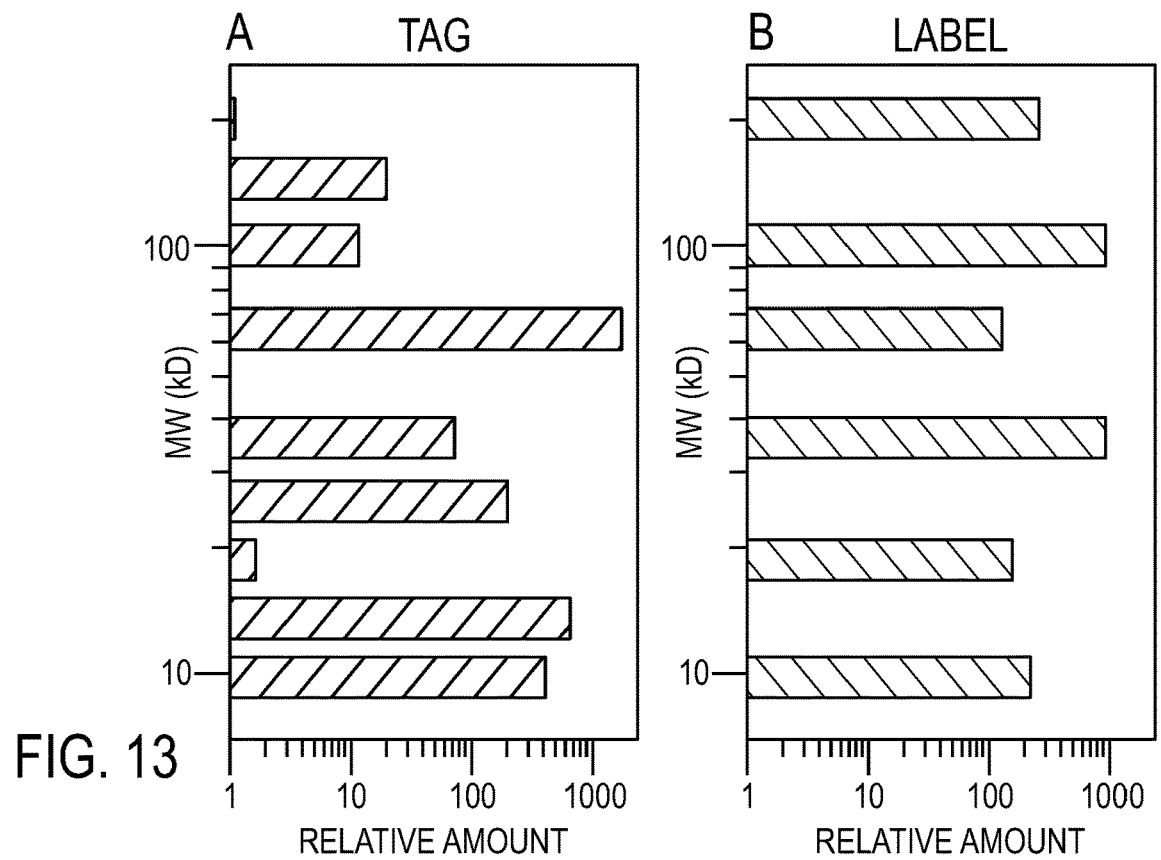
FIG. 13 is a pair of log-log bar graphs plotting, for still another exemplary reference composition, relative amounts of a tag present in a set of tagged quantitation standards (panel A) and relative amounts of a label incorporated into a set of labeled size markers (panel B), where only a subset of the tagged quantitation standards correspond in size to one of the labeled size markers.

Example 3. Reference Composition with More Quantitation Standards Than Size Markers This example describes a reference composition having a greater number of tagged quantitation standards than labeled size markers of different molecular weight; see FIG. 13.

The reference composition has nine tagged quantitation standards (see panel A) and six labeled size markers (see panel B). Each of the six labeled size markers substantially corresponds in molecular weight to one of the nine tagged quantitation standards. Three of the tagged quantitation standards do not correspond in molecular weight to any of the six labeled size markers. A reference composition with a greater number of quantitation standards than size markers allows the user to more accurately quantify sample proteins, using the larger number of quantitation standards.

Example 4. Reference Composition with No Size Overlap

Figure 14:
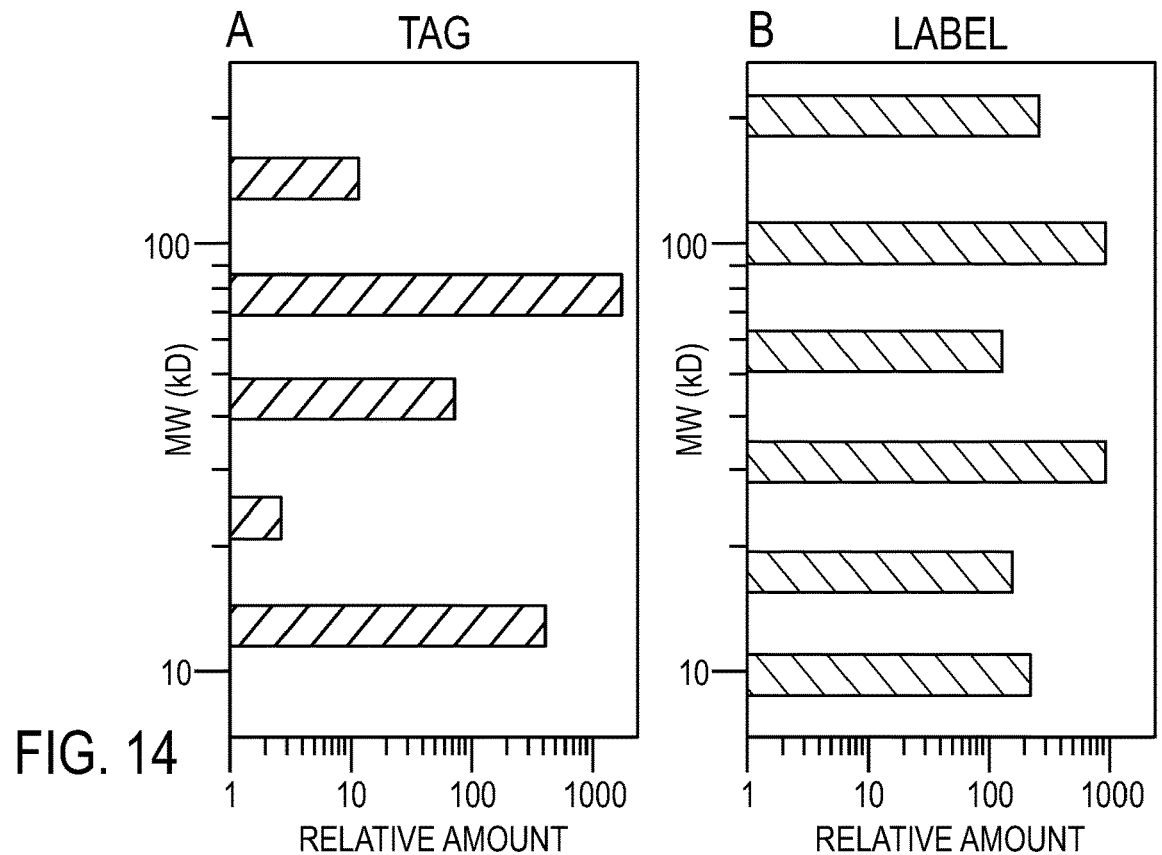
FIG. 14 is a pair of log-log bar graphs plotting, for yet another exemplary reference composition, relative amounts of a tag present in a set of tagged quantitation standards (panel A) and relative amounts of a label incorporated into a set of labeled size markers (panel B), where the sizes of the labeled size markers and the tagged quantitation standards do not correspond to one another.

This example describes a reference composition having a set of quantitation standards and a set of labeled size markers that are significantly different in molecular weight from one another; see FIG. 14.

The reference composition has five tagged quantitation standards (see panel A) and six labeled size markers (see panel B). None of the five tagged quantitation standards substantially corresponds in molecular weight to any of the six labeled size markers. A reference composition having quantitation standards that are resolved from each size marker during electrophoresis allows luminescence to be detected from the quantitation standards and the size markers without interference from one another. For example, photoluminescence may be detected first from the blot at the size markers, each of which may include a fluorescent tag. After contacting the blot with a photoluminescence reagent(s), photoluminescence then may be detected from the blot at the size markers and the quantitation standards. This strategy allows the size markers to be identified unambiguously before the quantitation standards are detectable.

Example 5. Standard Curves for Quantitation Standards

Figure 15:
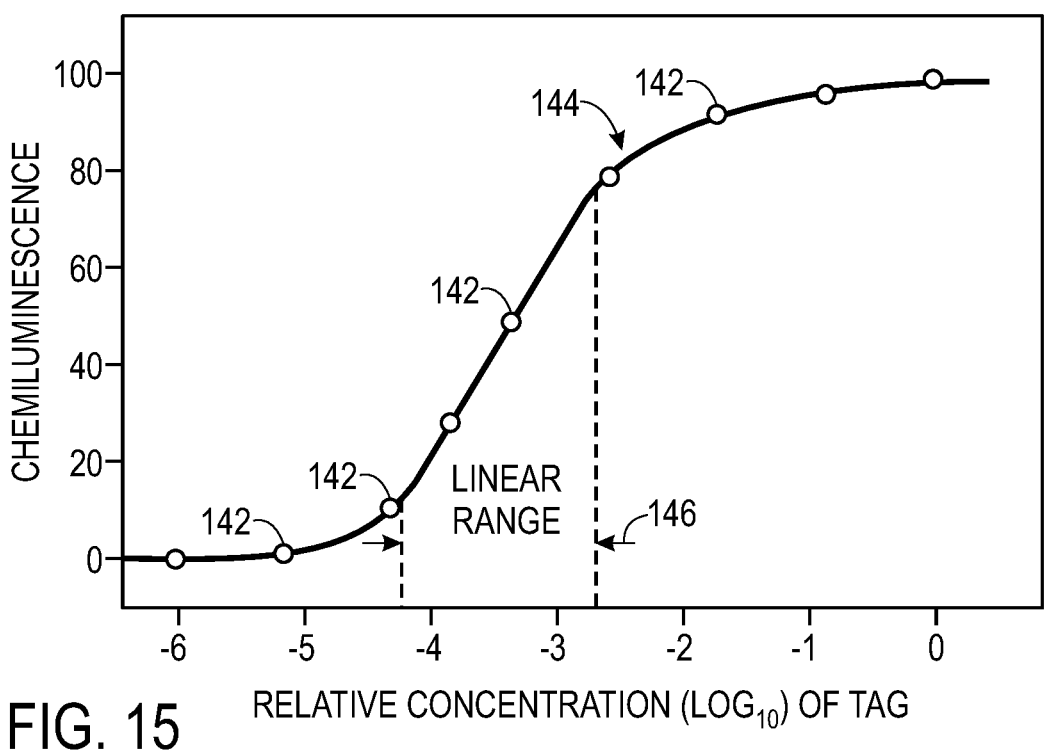
FIG. 15 is a graph plotting chemiluminescence that may be detected from a blot at a set of quantitation standards each including a tag, to produce a sigmoidal standard curve, where the largest and smallest concentrations of the tag differ by a factor of more than $10^6$, and where a linear range of the standard curve is demarcated by dashed vertical lines.
Figure 16:
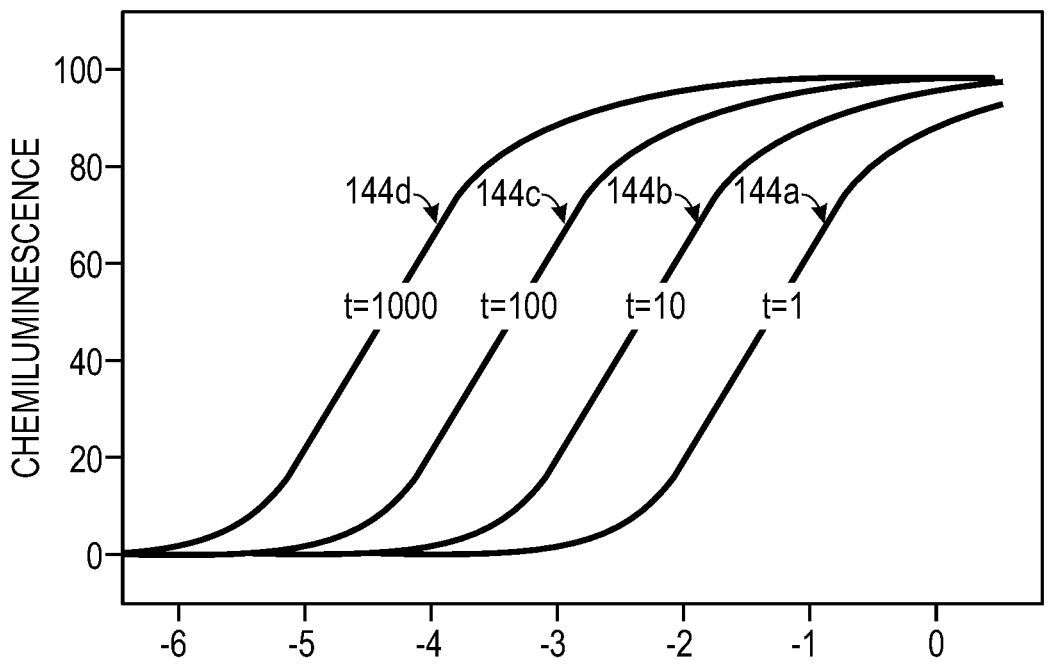
FIG. 16 is a graph plotting chemiluminescence that may be detected from the blot of FIG. 15 at the set of quantitation standards over different time periods (i.e., 1, 10, 100, and 1000 seconds), to produce a series of standard curves having linear ranges that are offset from one another but still overlapping.

This example describes standard curves that may be generated using a set of quantitation standards; see FIGS. 15 and 16.

FIG. 15 shows a graph plotting chemiluminescence (a luminescence response) that may be detected from a blot at each quantitation standard of a set of quantitation standards, indicated by points 142. The quantitation standards have respective tags of identical structure. The tags are used to bind a catalyst to each of the quantitation standards. The catalyst catalyzes a light-emitting chemical reaction that generates chemiluminescence at each quantitation standard (i.e., localized on the blot in very close proximity to the quantitation standard). The chemiluminescence detected for each quantitation standard is plotted as a function of the log(10) concentration of the tag. The largest and smallest concentrations of the tag differ by a factor of more than one million.

Points 142 define a standard curve 144 having a sigmoidal shape. Standard curve 144 has a linear portion defining a linear range 146 within which the standard curve is substantially linear. Below the linear range, the chemiluminescence is near or at background. Above the linear range, the chemiluminescence plateaus. Accordingly, for more accurate quantification of a sample protein using standard curve 144, the chemiluminescence detected from the blot at the sample protein should fall within linear range 146.

The blot of FIG. 15 also or alternatively may be used to calibrate the quantitation standards with respect to a known amount of the sample protein, if present on the blot. A chemiluminescence value obtained for the known amount of the sample protein, under the same conditions as the chemiluminescence values for standard curve 144, may be compared to standard curve 144 to obtain a conversion factor. The conversion factor may be used to convert the concentration (or amount) value of each quantitation standard to a quantity of the sample protein having luminescence equivalence to the quantitation standard. Luminescence equivalence means that the quantitation standard and the quantity of the sample protein are associated with the same level of luminescence.

FIG. 16 is a graph plotting chemiluminescence that may be detected from the blot of FIG. 15 at the quantitation standards for different amounts of time (i.e., 1, 10, 100, and 1000 seconds). The chemiluminescence values for the quantitation standards define a series of standard curves 144a-144d for the different amounts of time. The linear range of each standard curve is offset along the relative concentration axis from each other linear range. However, with proper selection of each time period, as shown, the linear ranges may overlap. For example, in the depicted embodiment, standard curves 140a-140d define a collective linear range that extends from −5 to −1 in the graph of FIG. 16, which is a difference of 10,000-fold. Accordingly, the series of standard curves can be used to quantify the sample protein over a range of 10,000-fold.

V. Selected Aspects

This section describes selected aspects of the methods and compositions of the present disclosure as a series of indexed paragraphs.

Paragraph A1. A method of quantifying a protein, the method comprising: (i) electrophoresing a reference composition and the protein in respective lanes of a gel, the reference composition including quantitation standards of different size each including a tag present at a different concentration; (ii) transferring the quantitation standards and the protein from the gel to a solid support to create a blot; (iii) detecting luminescence from the blot to obtain respective luminescence values separately representing an abundance of the tag of each quantitation standard and an abundance of the protein; and (iv) determining a quantity of the protein using the respective luminescence values.

Paragraph A2. The method of paragraph A1, the method further comprising determining whether the luminescence value for the protein falls within a linear range of luminescence response based on the luminescence values for the quantitation standards.

Paragraph A3. The method of paragraph A1 or A2, wherein detecting luminescence is performed using a non-destructive read sensor to capture a plurality of luminescence images representing luminescence detected from the blot for different amounts of time, wherein determining a quantity uses a first luminescence value obtained from a first luminescence image representing a shorter detection time and a second luminescence value obtained from a second luminescence image representing a longer detection time, and wherein the first luminescence value corresponds to a first quantitation standard having a higher concentration of the tag and the second luminescence value corresponds to a second quantitation standard having a lower concentration of the tag.

Paragraph A4. The method of any of paragraphs A1 to A3, wherein determining a quantity of the protein includes producing a standard curve using the luminescence values for the quantitation standards, identifying a point along a linear portion of the standard curve, the point having a luminescence value matching the luminescence value of the protein, and finding a quantity value associated with the point.

Paragraph A5. The method of any of paragraphs A1 to A4, the method further comprising determining a linear range of luminescence response as a function of tag abundance using the luminescence values for the quantitation standards, and determining whether the luminescence value for the protein falls within the linear range of luminescence response.

Paragraph A6. The method of any of paragraphs A1 to A5, wherein the quantitation standards are calibrated against a known amount of the protein, such that the luminescence value for the tag of each quantitation standard corresponds to a defined amount of the protein.

Paragraph A7. The method of any of paragraphs A1 to A6, wherein determining a quantity of the protein includes producing a standard curve using the luminescence values for the quantitation standards, wherein detecting luminescence is performed using an image sensor having a dynamic range, and wherein the standard curve encompasses a range of tag concentrations that is larger than the dynamic range of the image sensor (e.g., at least 2-, 5-, 10-, 20-, or 50-fold the dynamic range).

Paragraph A8. The method of any of paragraphs A1 to A7, wherein detecting luminescence includes detecting chemiluminescence representing each of the quantitation standards and the protein.

Paragraph A9. The method of any of paragraphs A1 to A8, wherein detecting luminescence includes detecting fluorescence representing each of the quantitation standards and the protein.

Paragraph A10. The method of any of paragraphs A1 to A9, wherein at least two of the tags of the quantitation standards differ in concentration by at least 100-fold.

Paragraph A11. The method of paragraph A10, wherein the at least two tags of the quantitation standards differ in concentration by at least 1000-fold.

Paragraph A12. The method of any of paragraphs A1 to A11, wherein the reference composition also includes a set of size markers each including a label that is chromophoric or fluorescent, and wherein each quantitation standard corresponds in size to one of the size markers.

Paragraph A13. The method of paragraph A12, wherein the label of each size marker is a chromophoric label, further comprising capturing an image representing absorbance of light by the chromophoric label of each size marker.

Paragraph A14. The method of paragraph A12, wherein the label of each size marker is a fluorescent label, further comprising capturing an image representing fluorescence of the fluorescence label of each size marker.

Paragraph A15. The method of paragraph A13 or A14, further comprising identifying an expected position of each quantitation standard on the blot based on positions of the size markers in the image.

Paragraph A16. The method of any of paragraphs A1 to A15, wherein the tags of the quantitation standards are structurally identical to one another.

Paragraph B1. A composition for protein quantification, comprising: a set of size markers configured to be resolved from one another in a gel to form a ladder representing a series of molecular weights, each size marker including a chromophoric or fluorescent label; wherein the composition includes three or more quantitation standards each having a tag, and wherein the tags of the three or more quantitation standards are present at predetermined concentrations defining a concentration range of at least 100-fold.

Paragraph B2. The composition of paragraph B1, wherein each quantitation standard corresponds in size to a different size marker of the set of size markers.

Paragraph B3. The composition of paragraph B2, wherein the tags of the three or more quantitation standards are present at ratios, relative to one another, that do not correlate with ratios, relative to one another, of the labels of the size markers to which the quantitation standards correspond in size.

Paragraph B4. The composition of any of paragraphs B1 to B3, wherein the size markers define a concentration range of less than 100-fold.

Paragraph B5. The composition of any of paragraphs B1 to B4, wherein each size marker of at least three of the size markers includes a mixture of non-tagged molecules lacking the tag and tagged molecules including the tag, wherein each of the non-tagged molecules and each of the tagged molecules includes the chromophoric or fluorescent label of the size marker, and wherein the non-tagged molecules outnumber the tagged molecules for each of the at least three size markers.

Paragraph B6. The composition of paragraph B5, wherein the non-tagged molecules are at least 100 times more abundant than the tagged molecules for at least one size marker of the at least three size markers.

Paragraph B7. The composition of any of paragraphs B1 to B6, wherein each size marker of at least three of the size markers includes an amino acid sequence of at least 100 amino acids that is present in one of the quantitation standards.

Paragraph B8. The composition of any of paragraphs B1 to B7, wherein the set of size markers defines a range of molecular weight including 20 kilodaltons and 80 kilodaltons.

Paragraph B9. The composition of paragraph B8, wherein the set of size markers defines a range of molecular weight including 15 kilodaltons and/or 150 kilodaltons.

Paragraph B10. The composition of any of paragraphs B1 to B9, wherein the set of size markers includes at least six size markers of different molecular weight.

Paragraph B11. The composition of any of paragraphs B1 to B10, wherein the three or more quantitation standards include at least six quantitation standards configured to be resolved from one another by gel electrophoresis.

Paragraph B12. The composition of any of paragraphs B1 to B11, wherein each size marker and each quantitation standard includes a polypeptide of at least 50 amino acids.

Paragraph B13. The composition of any of paragraphs B1 to B12, wherein the composition is an aqueous composition.

Paragraph B14. The composition of any of paragraphs B1 to B13, wherein the tags of the three or more quantitation standards are identical to one another structurally.

Paragraph B15. The composition of any of paragraphs B1 to B14, wherein the tag of each of the three or more quantitation standards is a peptide tag.

Paragraph B16. The composition of any of paragraphs B1 to B15, wherein the quantitation standards are present at predetermined concentrations defining a concentration range of at least 1000-fold.

The term "exemplary" as used in the present disclosure, means "illustrative" or "serving as an example." Similarly, the term "exemplify" (or "exemplified") means "to illustrate by giving an example." Neither term implies desirability or superiority.

While the invention has been described through the above examples and features, it will be understood by those of ordinary skill in the art that a wide variety of modifications, combinations and variations of the examples and features may be made without departing from the inventive concepts herein disclosed. Moreover, the invention should not be viewed as being limited to any specific purposes or embodiments described herein, but rather should be viewed as being applicable to accomplish a wide variety of purposes beyond those described herein. This disclosure describes some examples of the present technology with reference to the accompanying drawings, in which only some of the possible examples are shown. Other aspects can, however, be embodied in many different forms and should not be construed as limited to the examples set forth herein even if not expressly exemplified in combination. Rather, these examples were provided so that this disclosure is thorough and complete and fully conveys the scope of the possible examples to those skilled in the art.

We claim:

1. A method of quantifying a protein, the method comprising:
   electrophoresis reference composition and the protein in respective lanes of a gel, the reference composition including quantitation standards of different size each including a tag present at a different concentration;
   transferring the quantitation standards and the protein from the gel to a solid support to create a blot;
   detecting luminescence from the blot to obtain respective luminescence values separately representing an abundance of the tag of each quantitation standard and an abundance of the protein, wherein detecting luminescence is performed using plural luminescence images representing luminescence detected from the blot for different amounts of time; and
   determining a quantity of the protein using the respective luminescence values, wherein determining a quantity uses a first luminescence value obtained from a first luminescence image representing a shorter detection time and a second luminescence value obtained from a second luminescence image representing a longer detection time, and wherein the first luminescence value corresponds to a first quantitation standard having a higher concentration of the tag and the second luminescence value corresponds to a second quantitation standard having a lower concentration of the tag.

2. The method of claim 1, further comprising determining whether the luminescence value for the protein falls within a linear range of luminescence response based on the luminescence values for the quantitation standards.

3. The method of claim 1, wherein detecting luminescence is performed using a nondestructive read sensor.

4. The method of claim 1, wherein determining a quantity of the protein includes producing a standard curve using the luminescence values for the quantitation standards, identifying a point along a linear portion of the standard curve, the point having a luminescence value matching the luminescence value of the protein, and finding a quantity value associated with the point.

5. The method of claim 1, wherein the quantitation standards are calibrated against a known amount of the protein, such that the luminescence value for the tag of each quantitation standard corresponds to a defined amount of the protein.

6. The method of claim 1, wherein determining a quantity of the protein includes producing a standard curve using the luminescence values for the quantitation standards, wherein detecting luminescence is performed using an image sensor having a dynamic range, and wherein the standard curve encompasses a range of tag concentrations that is greater than the dynamic range of the image sensor.

7. The method of claim 1, wherein detecting luminescence includes detecting chemiluminescence representing each of the quantitation standards and the protein.

8. The method of claim 1, wherein detecting luminescence includes detecting fluorescence representing each of the quantitation standards and the protein.

9. The method of claim 1, wherein at least two of the tags of the quantitation standards differ in concentration by at least 100-fold.

10. The method of claim 9, wherein the at least two tags of the quantitation standards differ in concentration by at least 1000-fold.

11. The method of claim 1, wherein the reference composition also includes a set of size markers each including a label that is chromophoric or fluorescent, and wherein each quantitation standard corresponds in size to one of the size markers.

12. The method of claim 11, wherein the label of each size marker is a chromophoric label, further comprising capturing an image representing absorbance of light by the chromophoric label of each size marker.

13. The method of claim 1, wherein the tags of the quantitation standards are structurally identical to one another.

* * * * *